(12) United States Patent
Ishikawa et al.

(10) Patent No.: US 7,637,919 B2
(45) Date of Patent: Dec. 29, 2009

(54) ANASTOMOSIS SYSTEM FOR PERFORMING ANASTOMOSIS IN BODY

(75) Inventors: Masahiro Ishikawa, Hino (JP); Anthony Nicholas Kalloo, Glenn Dale, MD (US); Sergey Veniaminovich Kantsevoy, Silver Spring, MD (US)

(73) Assignee: Olympus Corporation, Tokyo (JP)

(*) Notice: Subject to any disclaimer, the term of this patent is extended or adjusted under 35 U.S.C. 154(b) by 191 days.

(21) Appl. No.: 10/353,865

(22) Filed: Jan. 29, 2003

(65) Prior Publication Data
US 2003/0216749 A1 Nov. 20, 2003

Related U.S. Application Data

(60) Provisional application No. 60/352,727, filed on Jan. 30, 2002.

(51) Int. Cl.
*A61B 17/11* (2006.01)
(52) U.S. Cl. .................................. 606/153; 606/108
(58) Field of Classification Search ............... 606/8, 606/10, 52, 205; 600/114, 129, 136, 153
See application file for complete search history.

(56) References Cited

U.S. PATENT DOCUMENTS

| | | | | |
|---|---|---|---|---|
| 2,127,903 A | * | 8/1938 | Bowen | 606/154 |
| 4,964,863 A | * | 10/1990 | Kanshin et al. | 606/153 |
| 5,425,738 A | | 6/1995 | Gustafson et al. | |
| 5,441,507 A | | 8/1995 | Wilk | |
| 5,813,973 A | * | 9/1998 | Gloth | 600/29 |
| 6,059,719 A | * | 5/2000 | Yamamoto et al. | 600/127 |
| 6,458,140 B2 | * | 10/2002 | Akin et al. | 606/153 |
| 7,175,644 B2 | * | 2/2007 | Cooper et al. | 606/191 |

FOREIGN PATENT DOCUMENTS

| | | |
|---|---|---|
| JP | 3-54603 | 5/1991 |
| JP | 6-47050 | 2/1994 |
| JP | 2000-37347 | 2/2000 |
| JP | 2000-166936 | 6/2000 |

* cited by examiner

*Primary Examiner*—Anhtuan T Nguyen
*Assistant Examiner*—Tuan V Nguyen
(74) *Attorney, Agent, or Firm*—Scully, Scott, Murphy & Presser, P.C.

(57) ABSTRACT

There is provided an anastomosis system for performing an anastomosis in a body. The system includes an anastomosis button, which has two foldable flange portions and a tubular main body portion extending between the flange portions, for coupling two lumen portions in the body to each other, and a housing which can receive the anastomosis button as the flange portions are folded. The system further includes a guide, which has a distal end to be inserted through a patient's mouth to a target portion in the body and a proximal end arranged outside the body, for guiding the housing to the target portion. A release line having a distal end to be inserted to the target portion along the guide and a proximal end held outside the body is operated, whereby the anastomosis button can be ejected from the housing and be held at the target portion.

7 Claims, 10 Drawing Sheets

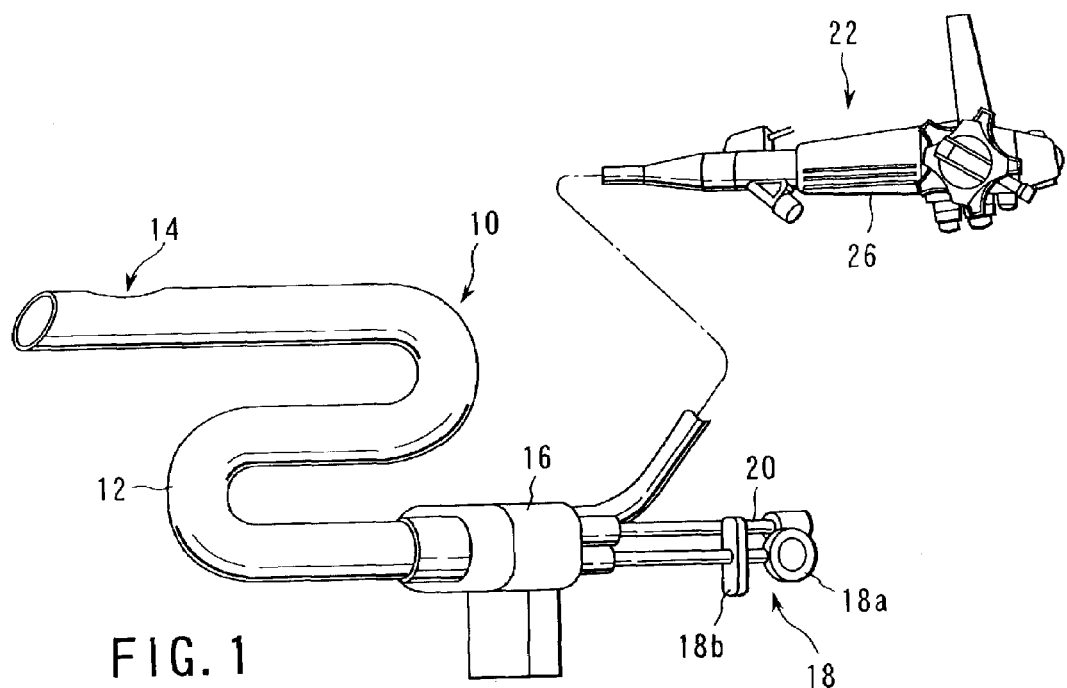
FIG. 1
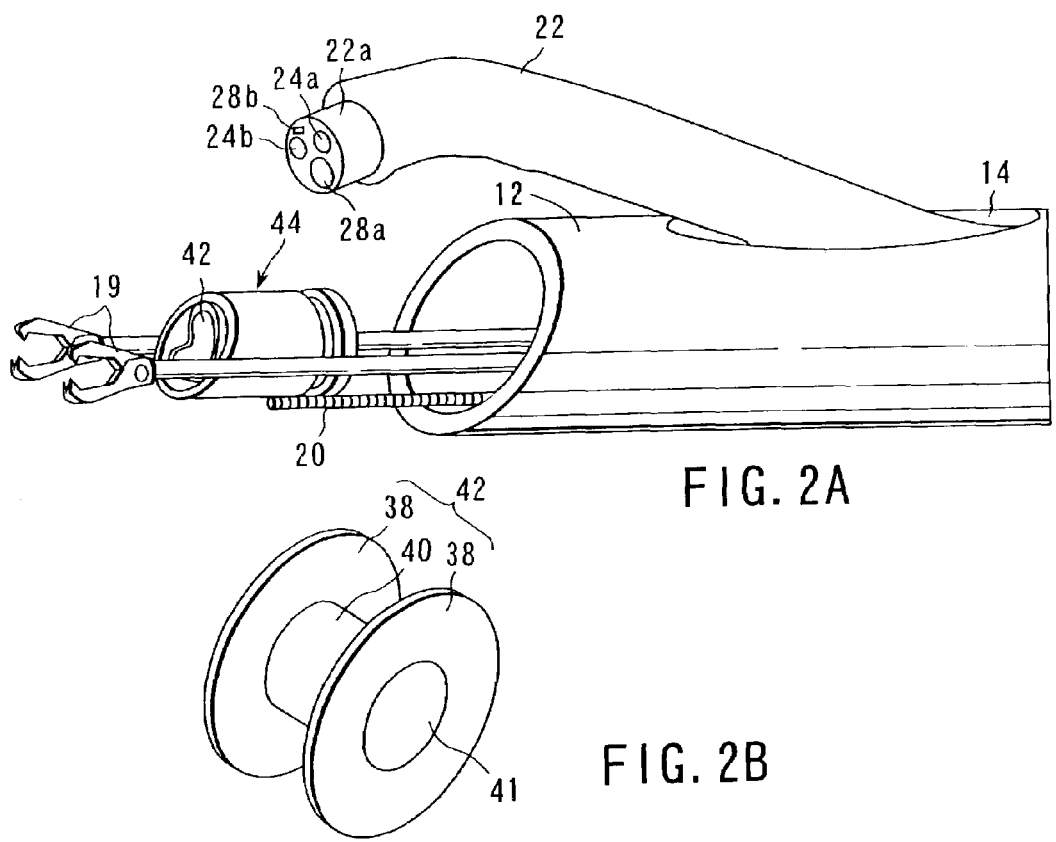
FIG. 2A
FIG. 2B

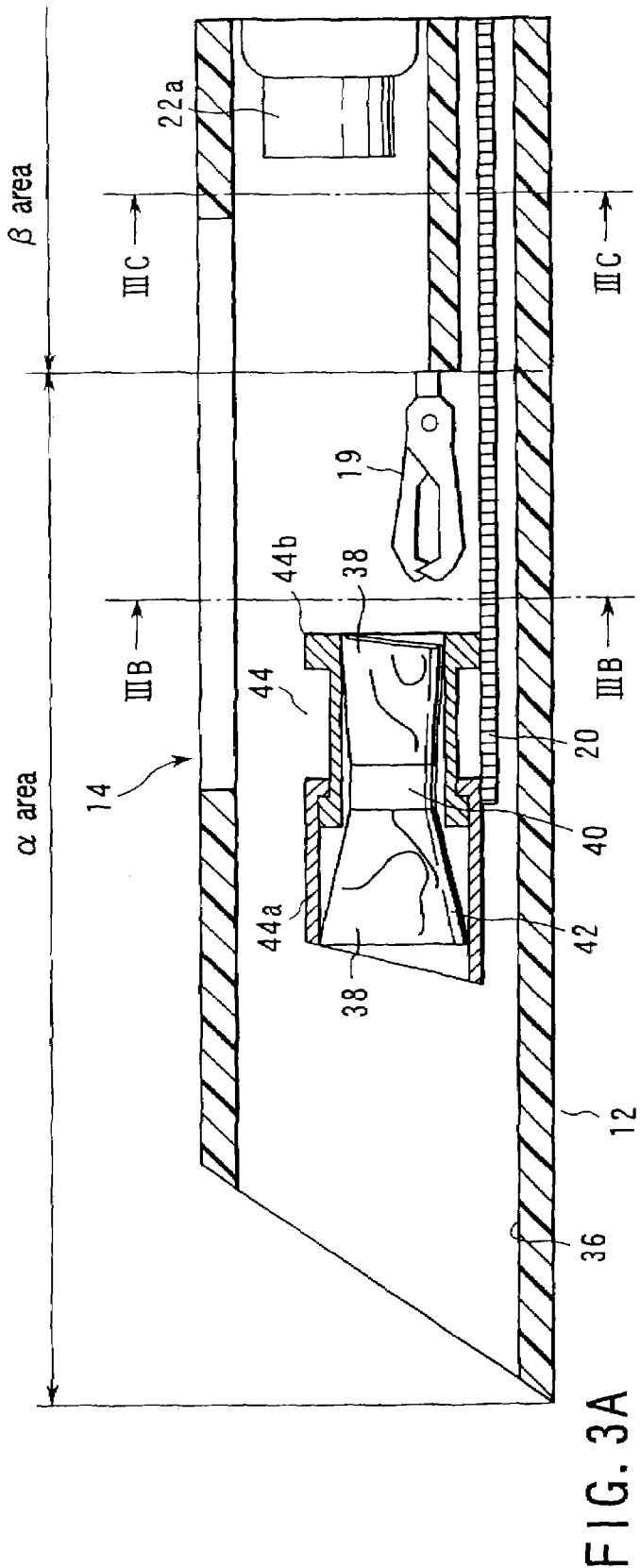
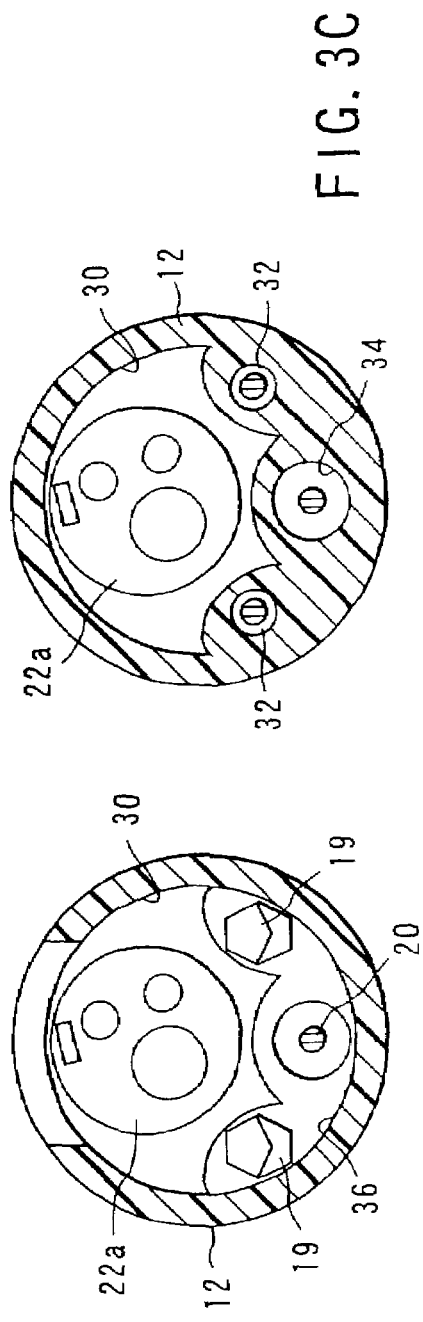
FIG. 3A
FIG. 3B
FIG. 3C

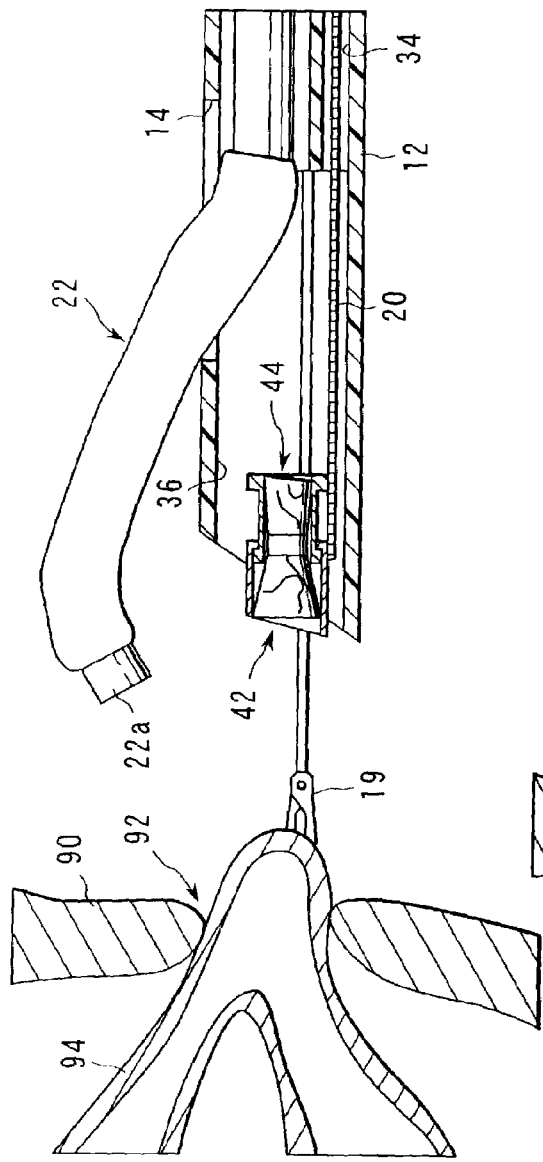
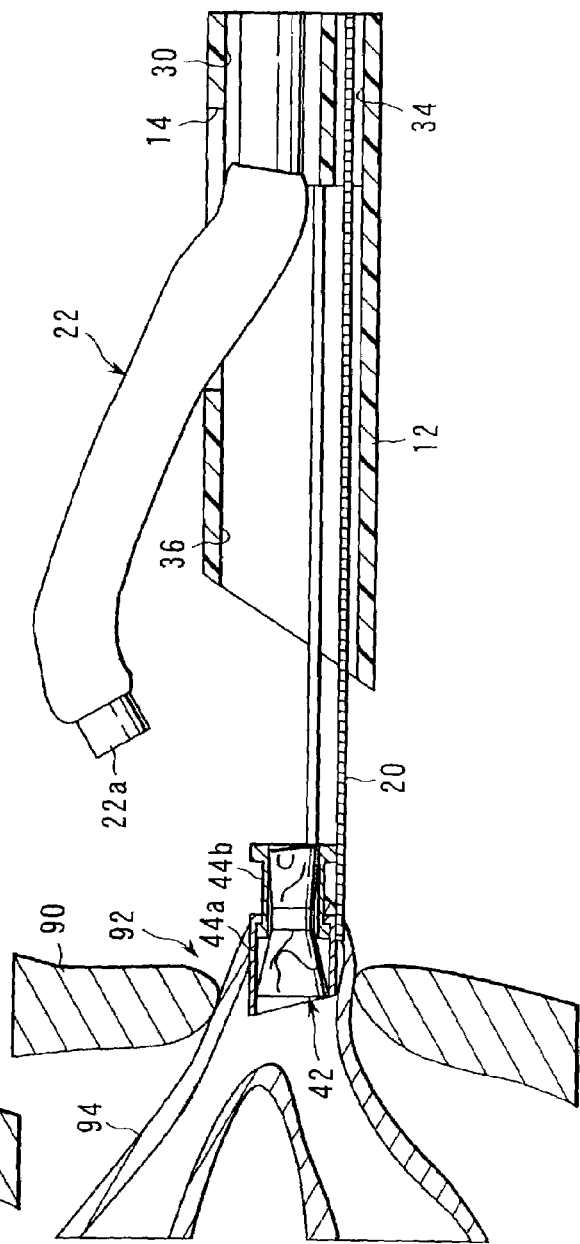
FIG. 4
FIG. 5

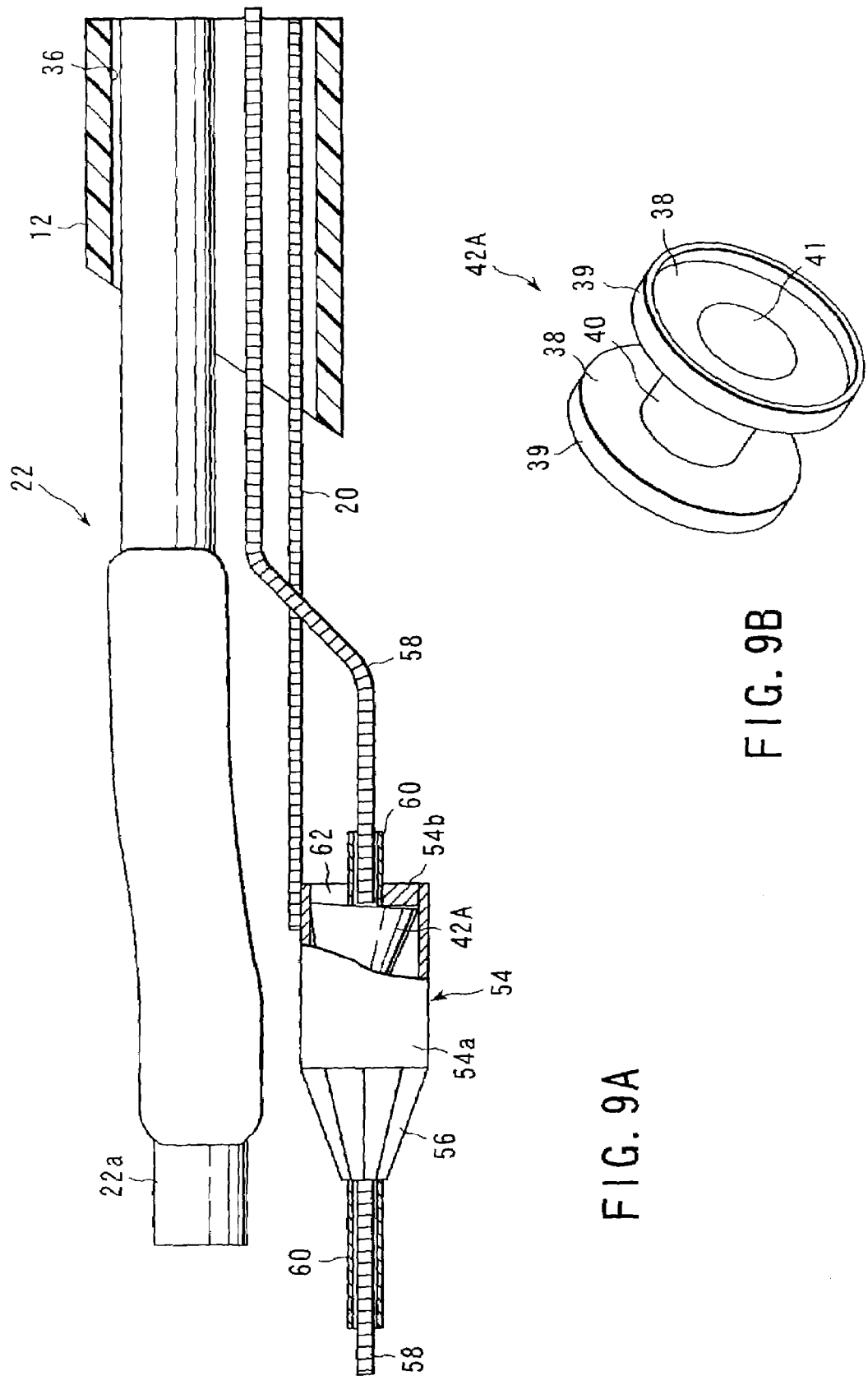

ANASTOMOSIS SYSTEM FOR PERFORMING ANASTOMOSIS IN BODY

CROSS-REFERENCE TO RELATED APPLICATIONS

This application claims the benefit of U.S. Provisional Application No. 60/352,727, filed Jan. 30, 2002.

BACKGROUND OF THE INVENTION

1. Field of the Invention

The present invention relates to an anastomosis system and, more particularly, to an anastomosis system used for, e.g., a gastrointestinal anastomosis to couple two organs or lumen portions in a living body to each other.

2. Description of the Related Art

In recent years, treatments using an endoscope have progressed remarkably, so that treatment can be accomplished without major surgery involving a large incise in the abdomen. Particularly, an anastomosis of tubular organs or blood vessels in the coelom is a very important technique upon treatment under observation via the endoscope. Accordingly, various treatment techniques using the endoscope have been developed.

For example, U.S. Pat. No. 5,425,738 discloses an endoscopic insertion device for inserting an anastomosis ring including two members, which can be engaged with each other, into a tubular tissue such as a blood vessel or a large intestine. The insertion device includes an outer sleeve which has a stop portion at its distal end and an obturator, which is inserted through the outer sleeve, and has an inflatable cuff at its distal end. In the state in which the cuff is partially inflated, the anastomosis ring can be inserted into the tubular tissue. After the tubular tissue is fixed to the members of the anastomosis ring, the members are closed to anastomose the tubular tissue fixed to the members.

U.S. Pat. No. 5,441,507 discloses a technique for anastomosing tubular organs under observation via an endoscope. According to the disclosed technique, one end of a first severed intestinal segment is purse-string sutured, an end cap of an anastomosis device is inserted into the first intestinal segment, and after that, the first intestinal segment is anastomosed to a second intestinal segment.

Furthermore, Jpn. Pat. Appln. KOKAI Publication No. 6-47050 discloses a tissue suture ligature device to be inserted to a tubular organ. The ligature device has an annular staple releasing section and an anvil opposite thereto. The anvil is axially moved to bend the legs of staples penetrating a tissue, thereby performing a suture.

The anastomosis ring disclosed in U.S. Pat. No. 5,425,738 has a relatively large diameter. Accordingly, after the abdomen is pierced, it is necessary to insert the ring through a formed orifice into a coelom. Accordingly, a plurality of orifices formed by piercing the abdomen are required to insert a celoscope in addition to the insertion device. In the technique disclosed in U.S. Pat. No. 5,441,507, the anastomosis ring is not used. However, since the anastomosis device is relatively large and hard, it is necessary to form a plurality of orifices in the abdomen. As to the ligature device disclosed in Jpn. Pat. Appln. KOKAI Publication No. 6-47050, since the ligature is accomplished by using the staples, it is difficult to reduce the diameter of the ligature device.

Accordingly, demanded is the development of an anastomosis system which is inserted together with an endoscope through the mouth or the anus into the coelom to further reduce the burden on a patient.

BRIEF SUMMARY OF THE INVENTION

The present invention is made in consideration of the related arts and it is an object of the present invention to provide an anastomosis system in which an anastomosis button is inserted through the mouth or the anus into the coelom to further reduce the burden on the patient.

To accomplish the above object, according to the present invention, the anastomosis system to perform an anastomosis in a body includes an anastomosis button, which has two foldable flange portions and a tubular main body portion extending between the flange portions for coupling two lumen portions in the body to each other. The anastomosis button is received in a housing as the flange portions are folded and is inserted through at least one of the mouth or the anus to a target portion in the body. A guide, which guides the housing to the target portion in the body, includes a distal end to be inserted into the body and a proximal end arranged on the outside of the body. To eject the anastomosis button from the housing inserted to the target portion in the body through the guide, the anastomosis button further includes a release line, which includes a distal end to be inserted to the target portion along the guide and a proximal end held on the outside of the body, for ejecting the anastomosis button from the housing to be held in the target portion by operating the proximal end on the outside of the body.

In the anastomosis through the anastomosis system, since the anastomosis button is received in the housing as the flange portions are folded, even when the flange portions of the anastomosis button are large, the constitution of the anastomosis button is compact upon insertion. When the anastomosis button is ejected from the housing by operating the release line on the outside of the body, the anastomosis button is returned to the original form, whereby the two lumen portions can be coupled to each other. The ejection of the anastomosis button from the housing can be surely disposed at a correct position under observation via the endoscope inserted through the guide.

According to another aspect of the present invention, there is provided an improved anastomosis for anastomosing two lumen portions in a body. The anastomosis includes the steps of: providing an anastomosis button, which includes two foldable flange portions and a tubular main body portion extending between the flange portions, for coupling the two lumen portions in the body to each other; receiving the anastomosis button in a housing as the flange portions are folded; inserting a multi-lumen tube through either the mouth or the anus until the distal end of the tube reaches a target portion in the body; inserting an endoscope into the tube; piercing a coelom wall and holding the corresponding coelom wall to be anastomosed with a forceps or a wire with a needle inserted through either the tube or the endoscope to pierce the corresponding organic wall under observation via the endoscope; ejecting the anastomosis button from the housing to insert the main body portion of the anastomosis button into the orifices of the two coelom walls previously pierced; and holding the two coelom walls between the two developed flange portions.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram showing the entire structure of an anastomosis system according to a preferred embodiment of the present invention;

FIG. 2A is a schematic diagram explaining the arrangement of members in the distal end of a guide tube of the anastomosis system in FIG. 1;

FIG. 2B is a perspective view showing a developed anastomosis button;

FIG. 3A is a sectional view showing an internal portion of the guide tube in FIG. 2A;

FIG. 3B is a cross-sectional view taken along a line B-B in FIG. 3A;

FIG. 3C is a cross-sectional view taken along a line C-C in FIG. 3A;

FIG. 4 is an explanatory diagram showing a state in which a part of an intestine is pulled into a stomach through a stomach wall pierced by the anastomosis system in FIG. 1;

FIG. 5 is an explanatory diagram showing a state in which, in the state shown in FIG. 4, the intestine is pierced and a housing is inserted thereto;

FIG. 9A is a sectional view showing a part of an anastomosis system according to another embodiment;

FIG. 9B is a schematic perspective view of an anastomosis button used in the anastomosis system in FIG. 9A;

DETAILED DESCRIPTION OF THE INVENTION

Figure 6:
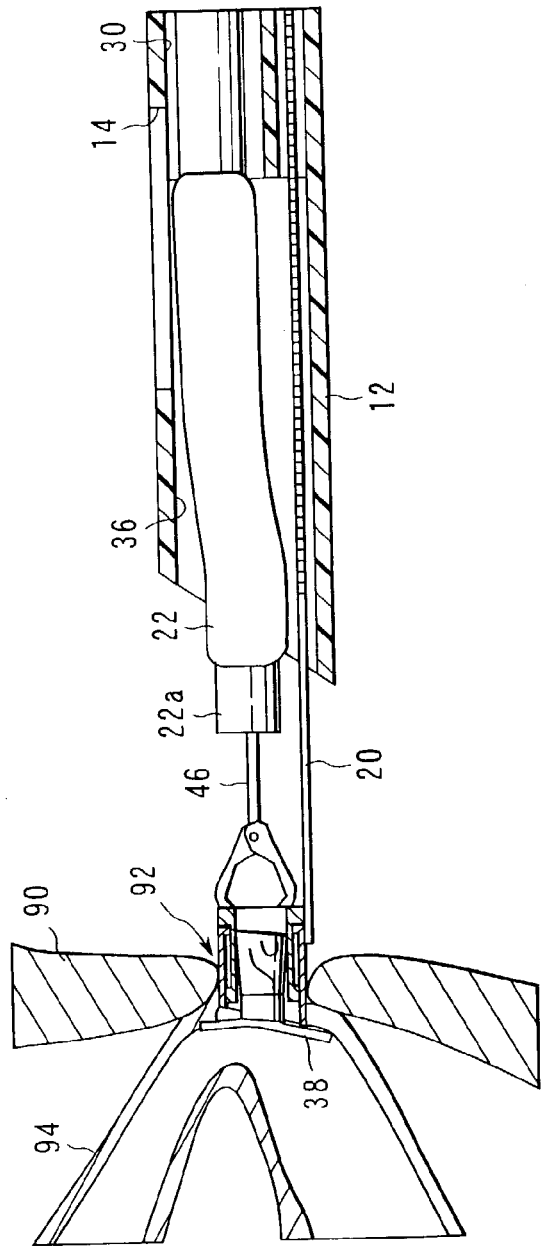
FIG. 6 is an explanatory diagram showing a state in which a part of the anastomosis button is ejected from the housing.

Referring to FIG. 1, an anastomosis system 10 according to a preferred embodiment of the present invention is suitable for a gastroenterostomy in a treatment for, particularly, obesity. The system is not limited thereto. The anastomosis system 10 has a guide 12 shaped into a flexible tube which can be inserted through a mouth. As to the guide 12 according to the present embodiment, at least its distal end is made of transparent resin. At the distal end to be inserted to the coelom, a plane at the distal end is inclined in the longitudinal direction of the axis. In the vicinity of the plane at the distal end, an orifice 14 to be opened on the side is formed. A holding instrument 18 such as a grasping forceps (in FIG. 1, only one is shown), a housing operation shaft 20 for operating a housing, which will be described below, and an endoscope 22 are inserted through an operation section main body 16 arranged on the outside of a body into the guide, so that the distal ends thereof are guided to a target portion in the coelom. Since at least the distal end of the guide 12 is made of the transparent resin, even when the distal end 22a of the endoscope 22 is not protruded from the guide 12, the coelom can be observed through the endoscope 22.

Referring to FIGS. 2A to 3C, the distal end 22a of the endoscope 22 inserted through the guide 12 can be protruded outwardly in the radial direction from the inside of the guide 12 through the side orifice 14 opened in the vicinity of the plane at the distal end of the guide 12. According to the present embodiment, therefore, illumination light guided through a light guide (not shown) is irradiated from an illumination window 24a, which is formed on the surface at the distal end 22a, to a predetermined portion in the coelom, so that reflected light incident on an observation window 24b can be guided to an endoscope operation section 26 arranged on the outside of the body through an image guide (not shown). Reference numeral 28a shown in FIG. 2A denotes a channel through which an operative instrument such as a forceps or a high-frequency knife is inserted. Reference numeral 28b denotes a nozzle for ejecting water or air.

Further, in the guide 12, a large-diameter lumen 30 through which the endoscope 22 is inserted and a plurality of small-diameter lumens 32 and 34 are formed. According to the present embodiment, through each of the small-diameter lumens 32, a shaft of the holding instrument 18 having, for example, a grasping forceps 19 at the distal end is inserted. The housing operation shaft 20 is inserted through the small-diameter lumen 34. As shown in FIGS. 3A to 3C, in the vicinity of the distal end of the guide 12, the lumens 30 to 34 constitute a common lumen 36 as a space with a large diameter. In FIG. 3A, reference symbol α designates an area where the common lumen 36 is formed and reference symbol β designates an area where the lumens are formed. The side orifice 14 is not always formed in the area α. Preferably, the orifice 14 is formed in the vicinity of the distal end of the guide 12.

In the area α formed as mentioned above, namely, the area where the common lumen 36 with a large diameter is formed, a housing 44 receiving an anastomosis button 42 having two flange portions 38 and a tubular main body portion 40 extending between the flange portions (refer to FIG. 2B) is arranged. Accordingly, the dimension of the common lumen 36 in the axial direction is preferably set so that the housing 44 can be received fully.

The anastomosis button 42 is made of a flexible or elastic material which can be deformed. Particularly, the flange portions 38 are folded to be received in the housing 44. When they are ejected from the housing 44, the flange portions 38 can be immediately returned to the original form. Moreover, as will be explained below, the anastomosis button 42 has such strength that, for example, when a stomach wall is anastomosed to an intestine wall, the two wall portions can be tightly held until they adhere to each other.

The housing 44 receiving the above-mentioned anastomosis button 42 is constituted of two cylindrical portions 44a and 44b which are engaged with each other in a telescopic manner in the present embodiment. Particularly as shown in FIG. 3A, the cylindrical portions 44a and 44b are formed so that the elongated cylindrical portions are substantially equivalent to the axial length of the anastomosis button 42 elongated in an hourglass-shaped form as the two flange portions 38 are folded oppositely. The operation shaft 20 is fixed to either one of the cylindrical portions 44a and 44b. According to the present embodiment, the end of the cylindrical portion 44a, which is located at the distal end of the housing 44, is tapered so as to be easily inserted into a pierced coelom wall. Since the sloped plane is formed at the distal end, when the anastomosis button 42 is ejected from the housing 44, the position of the anastomosis button 42 can be easily confirmed through the endoscope 22.

Subsequently, processing of, for example, a gastroenterostomy with the anastomosis system 10 will now be described.

As preparation before the operation, the anastomosis button 42 is folded in an hourglass-shaped form and is then stored in the elongated housing 44. The housing 44 receiving the anastomosis button 42 therein is disposed in the large-diameter common lumen 36 formed at the distal end of the guide 12. The operation shaft 20 is inserted through the lumen 34. As shown in FIG. 1, an operation section of the shaft is disposed on the outside of the operation section main body 16. If necessary, the holding instruments 18 having the grasping forceps 19 at the distal end are also received in the common lumen 36 at the distal end of the guide 12 and the shafts thereof are inserted to the lumens 32. The operator inserts their thumb into a ring shown by reference numeral 18a in FIG. 1 and then moves the thumb with respect to a slider 18b and the ring 18a, so that a pair of jaws of each grasping forceps 19 can be opened or closed.

Subsequently, the distal end of the guide 12 prepared as mentioned above is inserted into the stomach of a patient through their mouth and esophagus and is then disposed at a desired portion. The state can be confirmed via the endoscope 22 previously inserted in the lumen 30, the endoscope being inserted subsequent to the guide 12. Particularly, when the endoscope 22 is inserted together with the guide 12, the confirmation can be easily made because the guide 12 is made of the transparent material.

After the distal end of the guide 12 reaches the desired position, the distal end 22a of the endoscope 22 is extended outwardly through the side orifice 14 of the guide 12 and the end surface of the distal end is aimed to a portion 92 to be pierced (refer to FIG. 4) of the stomach wall 90. After that, an incision instrument such as a high-frequency knife is inserted through, for example, the channel 28a (FIG. 2A) in the endoscope 22 to pierce the portion 92. At that time, the desired portion is held or pulled by the grasping forceps 19 while the portion 92 to be pierced of the stomach wall 90 is monitored by the endoscope 22, so that the portion can be surely easily pierced.

FIGS. 4 through 8 show a processing of anastomosing a small intestine 94 to the above-mentioned pierced portion 92 of the stomach wall.

As shown in FIG. 4, the two grasping forceps 19 (FIG. 4 shows only one of them) are advanced from the guide 12 under observation via the endoscope 22 to grasp the small intestine 94 and pull it into the stomach through the pierced portion 92 formed in the stomach wall. The small intestine 94 is also pierced by the incision instrument such as a high-frequency knife inserted through the channel in the endoscope 22.

After that, as shown in FIG. 5, the operating section of the operation shaft 20 is operated outside the body to protrude the housing 44 from the distal end of the guide 12 and then insert the housing 44 through the pierced portion in the small intestine 94. When the cylindrical portion 44a at the distal end in which one of the flange portions 38 is received is inserted into the small intestine 94, the insertion of the housing 44 is stopped. When the housing 44 is protruded from the guide 12, the common channel 36 serves as a free space.

Figure 7:
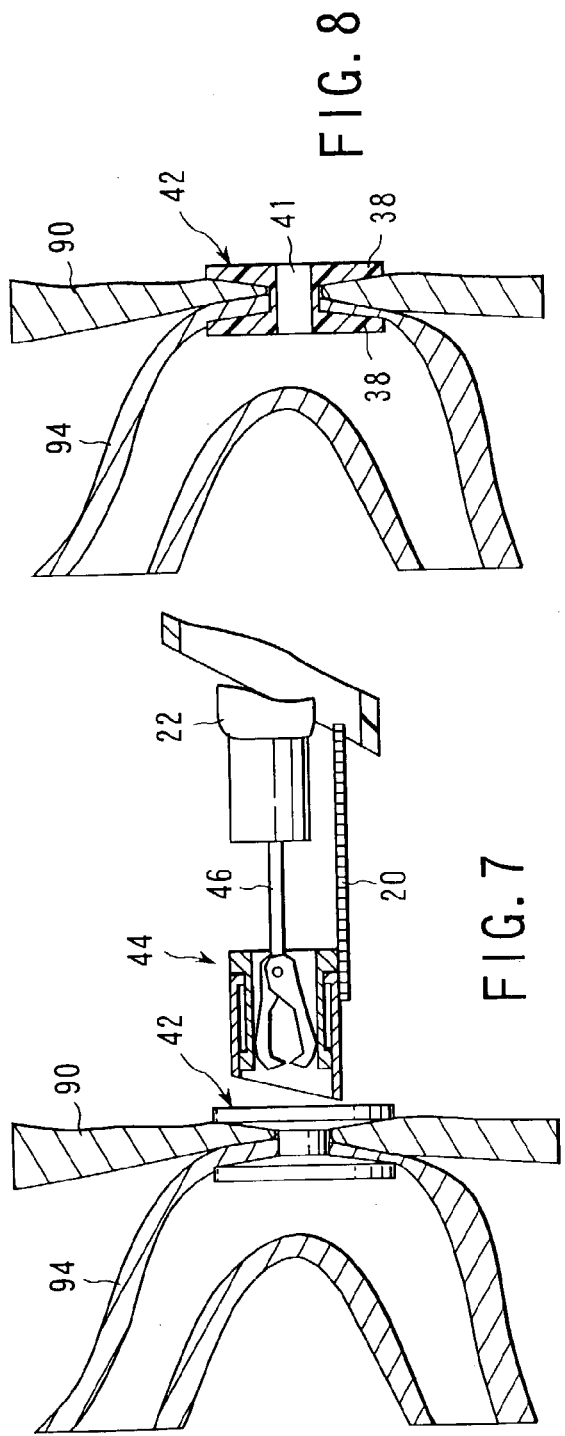
FIG. 7 is an explanatory diagram showing a state in which the ejection of the anastomosis button from the housing is completed.

As shown in FIG. 6, the distal end 22a of the endoscope 22 is inserted into the common channel serving as a free space. A release line illustrated by a grasping forceps 46 shown in FIG. 6 is advanced toward the housing 44 through the channel 28a in the endoscope 22. The operation shaft 20 or grasping forceps 46 is moved to telescope the cylindrical portions 44a and 44b of the housing 44, thereby extruding one of the flange portions 38 of the anastomosis button 42 into the small intestine 94. The flange portion 38 extruded in the small intestine 94 is returned to the original circular form by elasticity, so that the flange portion is brought into contact with the inner surface of the small intestine 94. Furthermore, when the operation shaft 20 is pulled out of the pierced portion 92 in the stomach wall 90 while the anastomosis button 42 in the housing 44 is retained by the grasping forceps 46 or release line, the other flange portion 38 is ejected from the housing 44 and is then returned to the original circular form by elasticity, so that the flange portion 38 is brought into contact with the inner surface of the stomach wall 90. FIG. 7 shows such a state.

Figure 8:
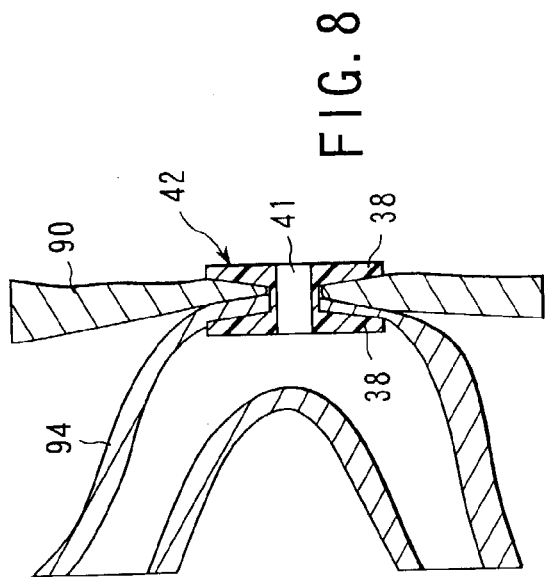
FIG. 8 is a sectional view showing a state in which the stomach wall and an intestine wall are subjected to the anastomosis with the anastomosis button.

Referring to FIG. 8, since the main body portion 40 of the anastomosis button 42 is shaped tubularly, two lumen portions of the stomach and the small intestine are coupled to each other through an orifice 41. Consequently, food fed to the stomach is immediately transferred to the small intestine 94, so that digestive and assimilative operations are not performed in the stomach. The anastomosis button 42 for anastomosing the stomach to the small intestine is held in the patient's body in this state for, e.g., about one week. After the pierced portions have adhered to each other, the button is extracted from the body. The anastomosis button 42, particularly, the flange portions 38 thereof are formed flexibly. Accordingly, when the flange portions 38 are grasped and then pulled by the grasping forceps, the anastomosis button can be easily removed from the pierced portion 92 in the stomach wall 90. The anastomosis button 42 can be easily removed by merely inserting the grasping forceps through the normal endoscope.

According to the anastomosis system 10 of the present embodiment, therefore, the anastomosis button 42 can be inserted together with the endoscope 22 through the mouth into the coelom. The gastroenterostomy can be performed remarkably easily. The patient is not burdened substantially. Moreover, since the housing 44 receiving the anastomosis button 42 therein is constituted of the remarkably simple cylindrical members, a special device is not needed, so that the anastomosis system is formed at extremely low cost.

FIGS. 9A through 12 show an anastomosis system according to another embodiment. Since the fundamental principle of the present embodiment described hereinafter is the same as that of the foregoing embodiment, the same components are designated by the same reference numerals and the detailed description is omitted.

As shown in FIG. 9A, a housing 54 according to the present embodiment includes a cylindrical portion 54a having a tapered distal end and a bottom wall portion 54b provided at the proximal end of the cylindrical portion. In the tapered end, at least one slit 56 is formed (it is preferable to form plural slits). Accordingly, the diameter of the tapered distal end can be enlarged. In the bottom wall portion 54b, a flexible guide tube 60, through which a guide wire 58 can be inserted, is fixed and an opening portion 62 is formed. The guide tube 60 is protruded from the distal end of the housing 54 so that it can guide the housing 54 while sliding along the guide wire 58 inserted therethrough. The housing 54 is held more surely than the case where the housing is held by the operation shaft 20 alone. The housing 54 is surely and easily guided to a desired position. An anastomosis button in the housing 54 is received on the guide tube 60.

As shown in FIG. 9B, in an anastomosis button 42A according to the present embodiment, a rim 39 is provided for the periphery of each flange portion 38 to increase the bending strength of the flange portion 38. Accordingly, even when the diameter of the penetrating orifice 41 is increased, the stomach wall 90 and the intestine wall 94 can be surely held without increasing the outer diameter or thickness of the flange portion 38. The rims 39 can be protruded so as to face each other. To allow the rims 49 to be smoothly in contact with the stomach wall 90 and the intestine wall 94, preferably, they are protruded opposite to each other as shown in FIG. 9B.

As shown in FIG. 9A, after the housing 54 according to the present embodiment is protruded from the common lumen 36 of the guide 12, it can be offset outwardly in the radial direction from the axis in the longitudinal direction of the guide 12 by the operation shaft 20 and the guide wire 58. Consequently, the distal end 22a of the endoscope 22 can be linearly advanced from the common lumen 36 of the guide 12 past the housing 54. In this case, it is unnecessary to form the side orifice 14 in the foregoing embodiment.

The anastomosis system according to the present embodiment can be used in a manner similar to the foregoing embodiment. According to the present embodiment, since the distal end 22a of the endoscope 22 can be linearly advanced past the housing 54, the stomach wall 90 and the intestine wall 94 can be pierced in a state in which the surface at the distal end of the endoscope is disposed substantially parallel to the walls.

Figure 10:
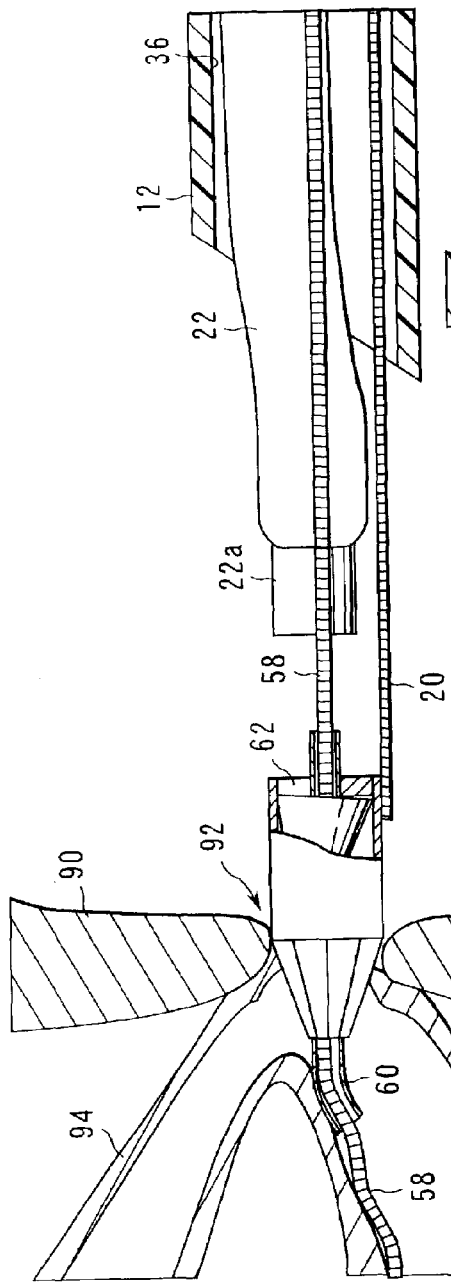
FIG. 10 is an explanatory diagram showing a state according to the anastomosis system in FIG. 9A, the state being similar to that in FIG. 5.

After the stomach wall 90 and the intestine wall 94 are pierced by a high-frequency knife, for example, the guide wire 58 can be inserted through the pierced portion before the housing 54 is inserted. Consequently, the housing 54 can be accurately and rapidly inserted through the pierced portion while the guide tube 60 is slid along the guide wire 58. In the case where the housing 54 is inserted through the pierced portion, since the distal end thereof is tapered, the housing 54 can be smoothly inserted into the small intestine even by a slight force. FIG. 10 shows the state in which the distal end of the housing 54 is inserted through the pierced portion.

Figure 12:
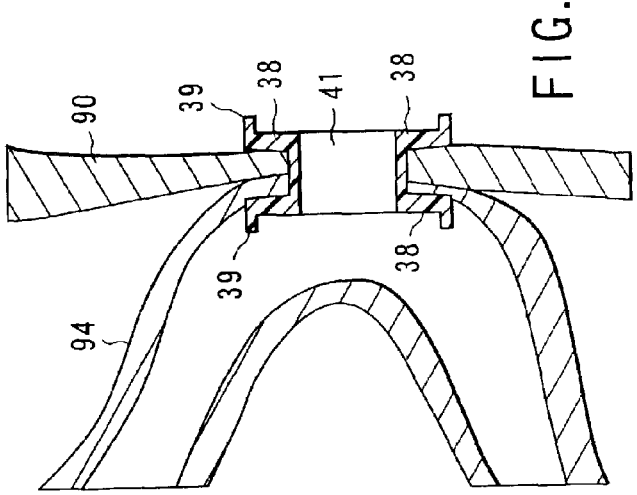
FIG. 12 is a sectional view showing a state in which an anastomosis is performed with the anastomosis button shown in FIG. 9B, the state being similar to that shown in FIG. 8.
Figure 11:
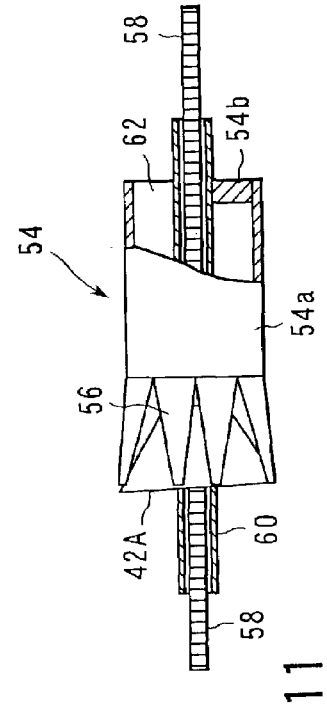
FIG. 11 is an explanatory diagram showing a state in which the anastomosis button is ejected from a housing in the anastomosis system in FIG. 9A.
Figure 20:
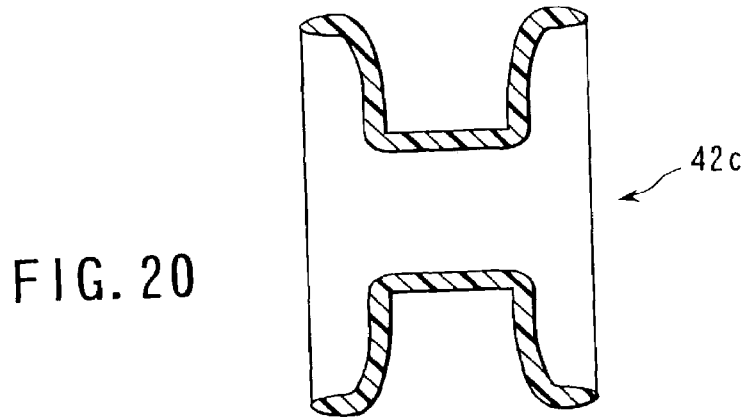
FIG. 20 is a sectional view of a modified anastomosis button.

When the anastomosis button 42A is ejected from the housing 54, the distal end of a release line such as a grasping forceps extending through the channel in the endoscope 22 is inserted into the housing 54 through the opening portion 62 formed in the bottom wall portion 54b. While the operation shaft 20 or the release line is being moved relatively, the anastomosis button 42A is moved to a front portion in the housing 54. Referring to FIG. 11, the slits 56 formed at the tapered distal end are opened to enlarge the diameter of the tapered distal end. When the flange portion 38 at the distal end of the received anastomosis button 42A is ejected from the housing 54, the flange portion 38 is spread and returned to the original circular shape due to elasticity, so that the flange portion 38 is brought into contact with the inner surface of the intestine wall 94. After that, when the operation shaft 20 and the guide wire 58 are pulled out of the anastomosis button 42A, the anastomosis button 42A is held to anastomose the small intestine to the stomach as shown in FIG. 12. The rim 39 protruded from the flange portion 38 prevents the flange portion 38 from bending. Accordingly, the rim 39 prevents the anastomosis button 42A from being detached from the pierced portion. FIG. 20 shows a modified button 42C with a rounded shape.

FIGS. 13 through 19 show further another embodiment.

Figure 13:
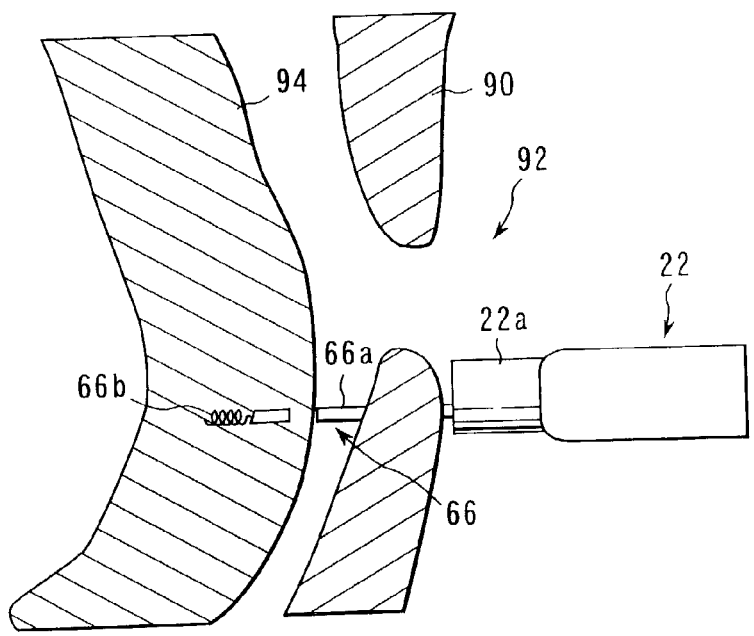
FIG. 13 is an explanatory diagram showing a state in which an intestine wall is held by a wire with a needle.

FIG. 13 shows a technique for pulling the intestine wall 94 of the small intestine in the present embodiment. In the technique, in stead of pulling the intestine wall 94 into the stomach through the pierced portion 92 in the stomach wall 90, the intestine wall 94 is drawn to the stomach wall 90 by a piercing needle 66 inserted through the channel 28a in the endoscope 22. The piercing needle 66 is formed as a long drawing line formed by inserting a needle wire 66b through a needle sheath 66a. The distal end of the needle wire 66b is coiled to form a needle portion. The needle wire 66b is inserted together with the needle sheath 66a into the intestine wall and the needle sheath 66a alone is removed. Consequently, the coiled needle at the distal end of the needle wire 66b is held in the intestine wall 94. Alternatively, the coiled needle pierces the intestine wall 94 to prevent the needle wire 66b from being removed from the intestine wall 94. In this state, the needle wire 66b is drawn in the direction toward the patient's mouth and is then fixed to an external portion of the body, so that it is possible to hold the state in which the intestine wall 94 is pulled to the stomach wall 90.

Figure 14A:
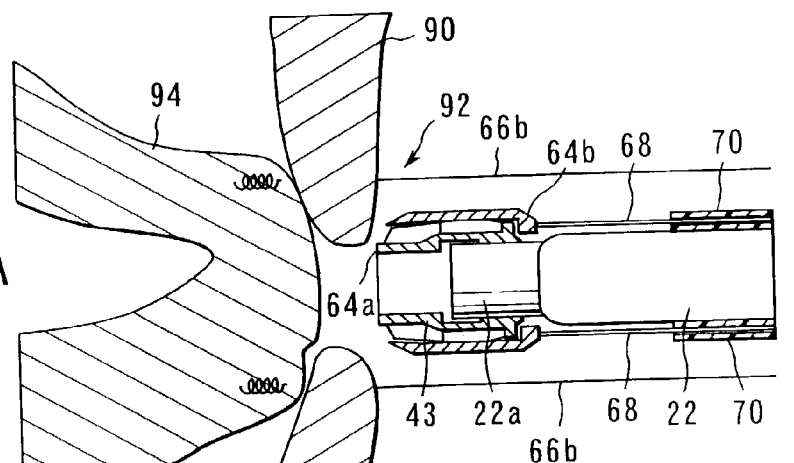
FIG. 14A is a sectional view showing a state in which an anastomosis is performed by using an anastomosis system according to further another embodiment.

As shown in FIG. 14A, ordinarily, it is preferable that the intestine wall 94 be drawn to the stomach wall 90 at portions opposite to the diameter of the pierced portion 92 by using two piercing needles 66.

Figure 14B:
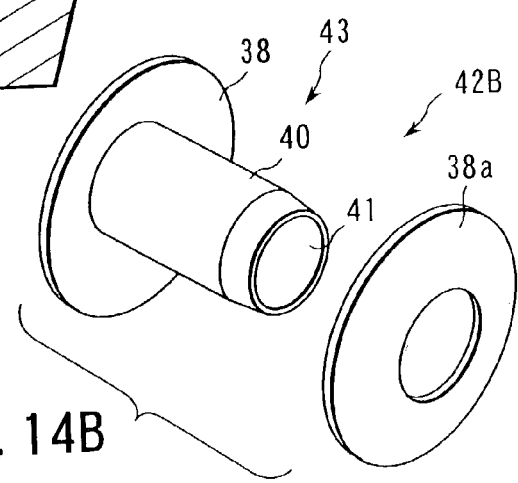
FIG. 14B is a schematic exploded perspective view of an anastomosis button used in the anastomosis system in FIG. 14A.

Furthermore, as shown in FIG. 14B, according to the present embodiment, an anastomosis button 42B is constituted of a first segment 43, which has the tubular main body portion 40 and the flange portion 38, and a second disc-like segment 38a that is fitted to the main body portion 40 of the first segment. The end of the main body portion 40 has a tapered shape so that the second segment 38a can be easily attached thereto. The second segment 38a is fitted to the first segment 43, thereby forming the flange portion opposite to the flange portion 38 of the first segment 43. The distance between the flange portions can be controlled in accordance with the thickness of the patient's stomach wall 90 and intestine wall 94. The entire anastomosis button 42B according to the present embodiment is round, so that it comes smoothly into contact with the stomach wall and the small intestine wall. The anastomosis button has a configuration that is friendly to a mucous membrane.

Figure 19:
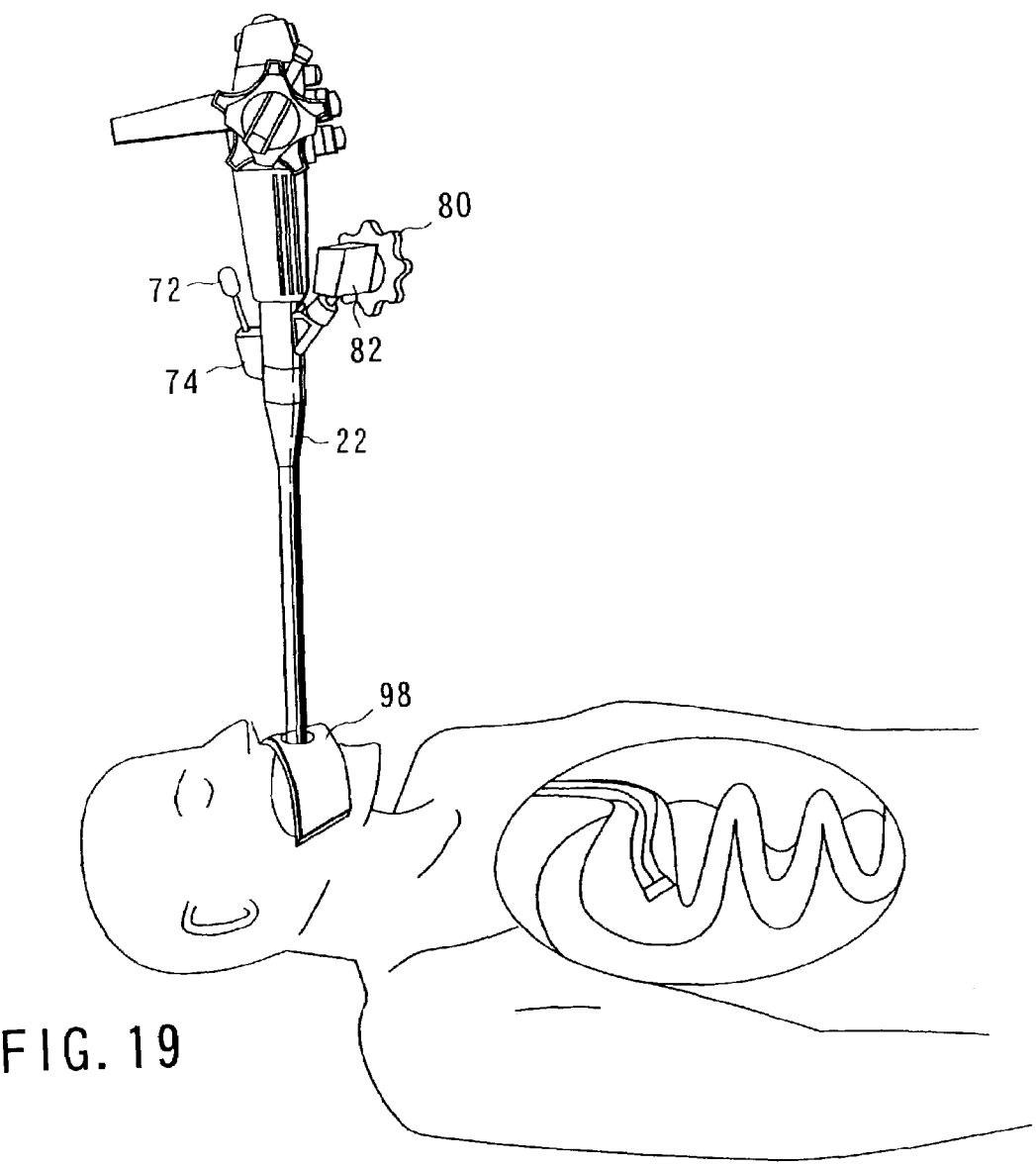
FIG. 19 is an explanatory diagram showing a state in which the anastomosis is performed by using the anastomosis system shown in FIG. 14A.

Referring to FIGS. 14A and 15 through 17, a housing 64 receiving the anastomosis button 42B therein has an inner cylindrical portion 64a that is attached to the distal end of the endoscope 22 and an outer cylindrical portion 64b that is slidably attached onto the inner cylindrical portion 64a. Between the two cylindrical portions, either the first segment or the second segment of the anastomosis button 42B is folded and they can be received. In the present embodiment, two operation wires 68 as release lines are connected to the outer cylindrical portion 64b. Each operation wire 68 is inserted through a tube sheath 70 and extends to an operation section of the endoscope 22 shown in FIG. 19. In FIG. 19, reference numeral 72 denotes an operation knob for the outer cylindrical portion which is connected to the operation wire 68 and reference numeral 74 denotes an operation main body for the outer cylindrical portion which is connected to the tube sheath 70.

Figure 16:
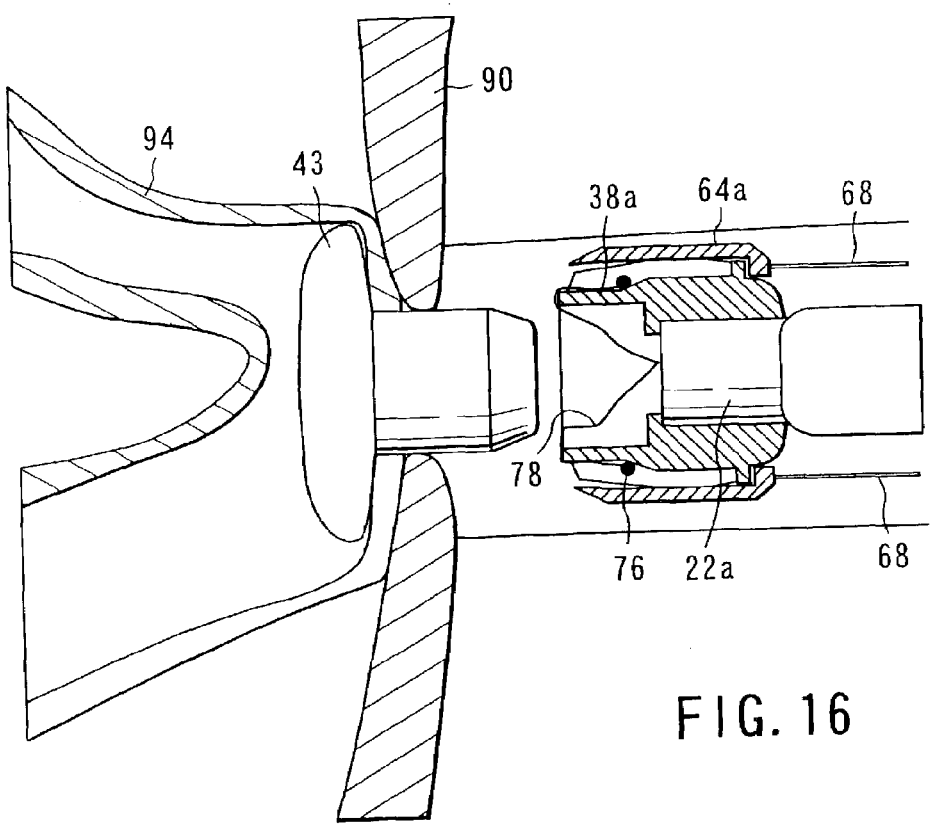
FIG. 16 is an explanatory diagram showing a state in which the other member of the anastomosis button is attached to the member, which is previously inserted.
Figure 17:
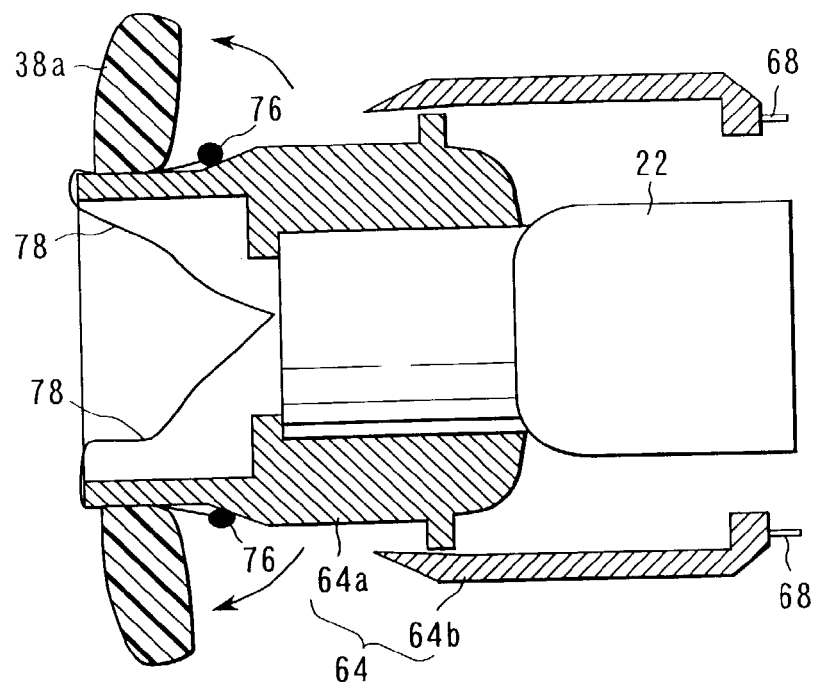
FIG. 17 is an explanatory diagram showing the ejection of the other member shown in FIG. 14B.
Figure 18:
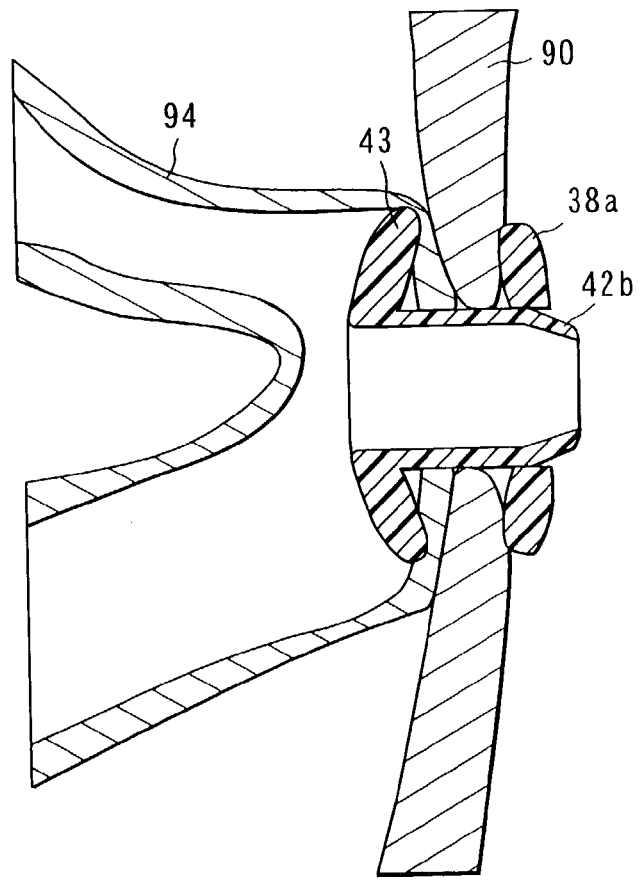
FIG. 18 is a sectional view showing a state in which the anastomosis is performed by the anastomosis button shown in FIG. 14B.

FIG. 14A shows a state in which the first segment 64a of the anastomosis button 42B is received. FIG. 16 shows a state in which the second segment 64b is received. As shown in the drawings, the housing 64 can receive the first segment 43 and the second segment 38a of the anastomosis button 42B in an annular gap between the inner and outer cylindrical portions 64a and 64b. In the case where the second disc-like segment 38a is received, as shown in FIGS. 16 and 17, button discharging threads 78 in which spherical beads 76 are connected to the distal ends are preferably used as release lines in addition to the operation wire 68.

Before the second segment 38a is attached onto the inner cylindrical portion 64a, the discharging thread 78 is inserted through the channel 28a in the endoscope 22 into the inner cylindrical portion 64a to dispose the beads 76 at both the distal ends on the outer peripheral surface of the cylindrical portion. After that, the second segment 38a is attached to the reduced diameter portion of the inner cylindrical portion 64a and is then covered with the outer cylindrical portion 64b. The proximal end of each discharging thread 78 extends outwardly from the operation section of the endoscope 22 and is then fixed to a button operation main body 82, which is rotated by a rotation knob 80, as shown in FIG. 19. The rotation knob 80 is rotated to wind the discharging threads 78 around the button operation main body 82. Consequently, the discharging threads 78 are pulled toward the proximal ends, so that the beads 76 discharge the second segment 74b out of the housing 64. Preferably, a plurality of discharge threads 78 are used as shown in FIGS. 16 and 17. One discharging thread can be also used.

The attachment of the anastomosis button 42B according to the present embodiment is performed as follows.

Referring to FIG. 14A, in the state in which the intestine wall 94 is drawn to the pierced portion 92 in the stomach wall 90, the endoscope 22 is inserted through a mouthpiece 98 (FIG. 19) attached to the patient's mouth. The distal end of the endoscope 22 is disposed opposite to the pierced portion 92 and the intestine wall 94 is pierced by an incision instrument such as a high-frequency knife inserted through the channel in the endoscope 22. At that time, although the housing 64 is attached to the distal end 22a, it does not disturb the piercing operation because the housing 64 has a cylindrical shape.

Figure 15:
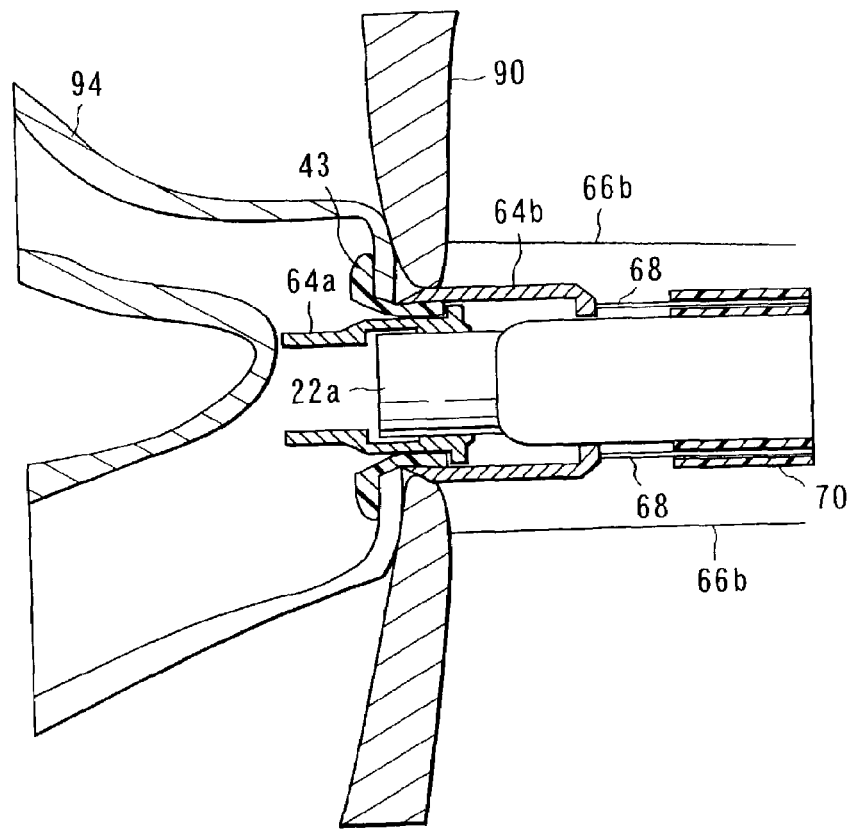
FIG. 15 is an explanatory diagram showing the insertion of a member of the anastomosis button shown in FIG. 14B.

Subsequently, referring to FIG. 15, the distal end of the housing 64 is inserted through an orifice formed in the intestine wall 94 and the operation knob 72 for the outer cylindrical portion 64b shown in FIG. 19 is drawn to move the outer cylindrical portion 64b backward. Consequently, the first segment 43 of the anastomosis button 42B is exposed and the flange portion 38 is developed in the original circular shape due to elasticity. After that, the endoscope 22 is withdrawn to pull the inner cylindrical portion 64a of the housing 64 out of the first segment 43. At that time, since the flange portion 38 is brought into contact with the inner surface of the intestine wall 94, the first segment 43 is held in the small intestine.

Subsequently, as shown in FIG. 16, the endoscope 22, in which the housing 64 receiving the second disc-like segment 38a is attached to the distal end 22a, is inserted into the stomach to allow the distal end to face the first segment 43 of the anastomosis button previously attached. The housing 64 is allowed to coaxially match the end, in which the diameter is reduced, of the main body portion 40 of the first segment 43 and is then close thereto. After that, the outer cylindrical portion 64b of the housing 64 is withdrawn and the rotation knob 80 provided for the operation section of the endoscope 22 is rotated to wind the discharging threads 78 around the button operation main body 8. Consequently, as shown in FIG. 17, the second segment 38a is returned to the original disc shape on the inner cylindrical portion 64a and is then discharged by the beads 76 to be attached onto the main body portion 40 of the first segment 43. In this instance, the first segment 43 can be held by a grasping forceps (not shown) inserted through the channel in the endoscope 22.

Since the present embodiment has been explained in association with the gastroenterostomy, the example in which the anastomosis button was inserted through the mouth has been described. Optionally, in accordance with a portion to be anastomosed, it is obvious that the anastomosis button can be inserted through the anus. The members in the embodiments can be properly combined to each other and they are not limited to any embodiment.

Consequently, according to the anastomosis system 10 of the above-mentioned embodiments, since the anastomosis button can be easily inserted through the mouth or the anus into the coelom, the burden on the patient is extremely little. Moreover, since it takes a remarkably short time, the system can be generally used in other applications in addition to the above-mentioned gastroenterostomy.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An anastomosis system for performing a gastrojejunostomy in a body, comprising:
    an anastomosis button, which includes two elastic and foldable circular flange portions and a tubular main body portion extending between the flange portions, to couple two lumen portions in the body to each other each of the flange portions having a circular form with a rim to increase bending strength;
    a housing in which the anastomosis button can be received as the flange portions are folded, wherein the housing comprises two cylindrical members, which relatively move axially to stepwise eject the anastomosis button;
    a guide which includes a distal end to be inserted through at least one of a mouth and an anus to a target portion in the body and a proximal end arranged on the outside of the body and which guides the housing to the target portion;
    incising means for incising a lumen wall of the target portion and a counterpart lumen wall to be anastomosed;
    inserting means for inserting one end of the housing via an incision formed in the lumen wall of the target portion into an incision formed in the counterpart lumen wall to be anastomosed;
    ejecting means for ejecting the anastomosis button from the housing; and
    expanding means for expanding the flange portions of the anastomosis button to be greater in diameter as compared to the housing, thereby holding the two lumen walls between the two flange portions.

2. The anastomosis system according to claim 1, wherein the guide comprises a flexible multi-lumen tube including at least a lumen through which an endoscope is inserted and a lumen through which the release line is inserted.

3. The anastomosis system according to claim 2, further comprising:
   an operation shaft which has a distal end supporting the housing and a proximal end arranged on the outside of the body,
   the tube further comprising a lumen through which the operation shaft is inserted and a large-diameter space which is formed at the distal end and which receives the housing,
   the lumens through which the endoscope, the release line, and the operation shaft are inserted, respectively, being terminated in the large-diameter space, and
   the distal end of the housing and the distal end of the release line protruding outwardly from the large-diameter space.

4. The anastomosis system according to claim 2, wherein the tube further comprises an orifice through which the distal end of the endoscope protrudes outwardly in the radial direction from the inside.

5. The anastomosis system according to claim 1, further comprising:
   a pulling line which has a distal end to be inserted to the target portion along the guide and a proximal end arranged on the outside of the body and which pulls an organic tissue in the vicinity of the target portion.

6. The anastomosis system according to claim 1, wherein at least a portion in the vicinity of the distal end of the guide is made of a transparent material.

7. The anastomosis system according to claim 1, further comprising an operation shaft which has a first end connected to the housing and a second end extending from the first end toward the proximal end of the guide, the operation shaft being inserted in the guide to allow movement relative to the guide so that the housing is movable between a first position in which the housing is held in the guide and a second position in which the housing is projected out of the distal end of the guide.

* * * * *